United States Patent
Faizan et al.

(10) Patent No.: US 11,891,221 B2
(45) Date of Patent: Feb. 6, 2024

(54) BIO-DEGRADABLE CONTAINER

(71) Applicant: Mirza Faizan, Irving, TX (US)

(72) Inventors: Mirza Faizan, Irving, TX (US); Mirza Rizwan, Patna (IN); Hana Ahmad, Allen, TX (US); Humza Ahmad, Allen, TX (US); Mohsen Ahmad, Allen, TX (US); Rabiya Sayeed, Murphy, TX (US); Sofia Ali, Garland, TX (US); Zain Ali, Garland, TX (US); Sarah Nawab, Dallas, TX (US); Danyal Nawab, Dallas, TX (US)

( * ) Notice: Subject to any disclaimer, the term of this patent is extended or adjusted under 35 U.S.C. 154(b) by 371 days.

(21) Appl. No.: 17/339,463

(22) Filed: Jun. 4, 2021

(65) Prior Publication Data

US 2022/0388736 A1     Dec. 8, 2022

(51) Int. Cl.
| | |
|---|---|
| B65D 47/12 | (2006.01) |
| C12N 1/14 | (2006.01) |
| B65D 17/34 | (2006.01) |
| B65D 43/02 | (2006.01) |
| B65D 51/28 | (2006.01) |
| B65D 65/46 | (2006.01) |

(52) U.S. Cl.
CPC ........... *B65D 47/122* (2013.01); *B65D 17/34* (2018.01); *B65D 43/02* (2013.01); *B65D 51/28* (2013.01); *B65D 65/466* (2013.01); *C12N 1/14* (2013.01)

(58) Field of Classification Search
None
See application file for complete search history.

(56) References Cited

U.S. PATENT DOCUMENTS

| | | | | |
|---|---|---|---|---|
| 2008/0041810 A1* | 2/2008 | Itoh | ............ | B65D 41/3428 215/316 |
| 2015/0298868 A1* | 10/2015 | Frishman | ........... | B65D 17/4012 215/250 |

* cited by examiner

*Primary Examiner* — Lee E Sanderson

(57) ABSTRACT

Biodegradable bottle cap is a water bottle cap containing the plastic eating fungus pestalotiopsismicrosporia. When the consumer is done drinking from the bottle, the cap has a tab that is pulled and this tab releases the fungus. The fungus consumes the plastic bottle and the cap so no trace is left behind. The cap is made of plastic and the fungus is contained in an aluminum casing. Also contain in the casing is the safe food dye which will be coloring the water in case of accidental release or opening of the casing before the use of the drinking water. Such water coloring will be an indication to avoid using the water for drinking though the fungus is safe after human galloping.

12 Claims, 3 Drawing Sheets

BIO-DEGRADABLE CONTAINER

FILED OF THE INVENTION

This invention relates to a container and more specifically to a biodegradable container for storing products.

BACKGROUND

In the global space, plastic packaging is now very commonly used for many products including semi-solid and liquid items such as food, beverages, water, consumer products, lotions, medicines, wet chemicals, and the like. However, these plastic packaged products generate waste in the form of plastics. Also these plastics contribute to release of various toxic substances into the dumped place.

Furthermore, most of the people, after using these plastic products, throw away these products into the public places, as water bodies, roads, and the alike. This further leads to endangering the water species and animals on the roads, in addition to the environment.

For this, paper containers are sometimes used instead to package liquids. But, the paper product assemblies have multiple seams and other potential weak points that may rupture or otherwise leak. These paper containers may also include additional materials such as plastic films or composite sheets that are not biodegradable.

Hence, there remains a need for a biodegradable container that may be destroyed automatically after usage.

SUMMARY

An embodiment is directed to bio-degradable container. The bio-degradable container comprising a body. The bio-degradable container further comprising a lid. The lid comprising an upper cover; a pullable seal tab of a pre-determined length. Further a pullable face of the pullable seal tab protrudes the upper cover. Further the lid comprising a breakable casing on a lower side of the upper cover. The breakable casing comprises a first segment and a second segment. Further, the lid comprising a lower cover. The inner portion of the lower cover engages the pullable seal tab with the breakable second casing to release a first pigment and a second pigment to bio-degrade the container.

In addition to one or more of the features described above or below, or as an alternative, wherein the body further comprises a base portion.

In addition to one or more of the features described above or below, or as an alternative, wherein an inner portion of the lid has a spiral wrap construction.

In addition to one or more of the features described above or below, or as an alternative, wherein the first segment houses the first pigment.

In addition to one or more of the features described above or below, or as an alternative, wherein the first pigment is a color pigment.

In addition to one or more of the features described above or below, or as an alternative, wherein the second segment houses the second pigment.

In addition to one or more of the features described above or below, or as an alternative, wherein the second pigment is a bio-degrading agent.

In addition to one or more of the features described above or below, or as an alternative, wherein the breakable casing is a plastic casing.

In addition to one or more of the features described above or below, or as an alternative, wherein the pullable seal tab is further configured to lock the body.

In addition to one or more of the features described above or below, or as an alternative wherein the lock of the body is actuated by pulling of the pullable seal tab.

OBJECTS OF THE INVENTION

The objective of the disclosed invention is to provide a bio-degradable container.

Yet another objective of the disclosed invention is to provide a safe bio-degradable container with a pull mechanism.

Yet another objective of the disclosed invention is to provide aluminum casing for storing second pigment to act as an agent for bio degrading.

Yet another objective of the disclosed invention is to provide aluminum casing for storing first pigment to change the color of the leftover liquid.

Yet another objective of the disclosed invention is to provide a bio-degradable container which may get automatically degrade upon release of the first pigment and the second pigment.

SHORT DESCRIPTION OF THE DRAWINGS

DETAILED DESCRIPTION OF THE DRAWINGS

Figure 1:
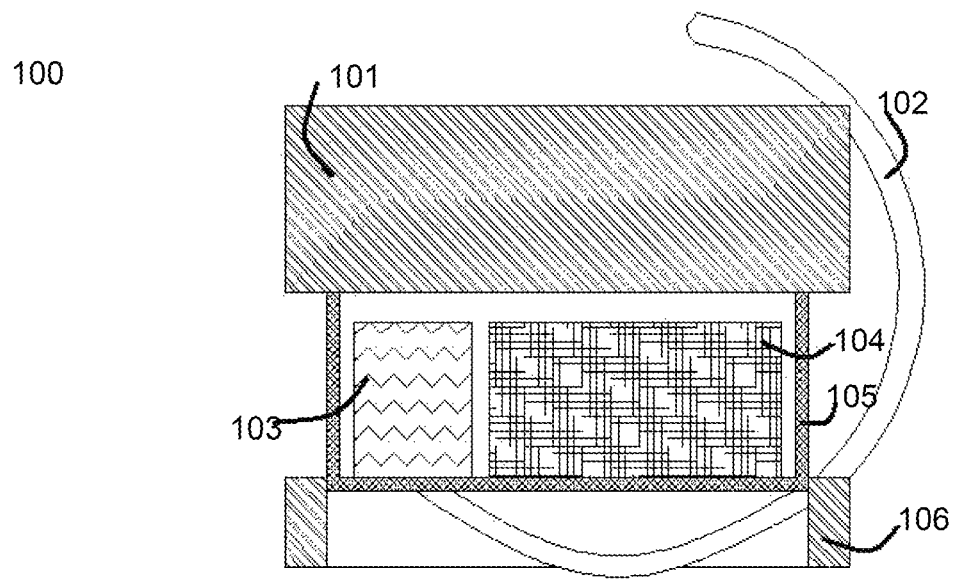
FIG. 1 depicts various sections of a lid, in accordance with various embodiments of the present invention.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions

The following terms shall have, for the purposes of this application, the respective meanings set forth below.

A "Container" refers to a carriage that may be a bottle for storage and transport of liquid items such as water, beverages, and the alike. In an embodiment of the present invention, the container may correspond to a round shaped, square shaped carriage which may be configured to storage and transport of liquid items.

A "Bio-degradable" refers to capable of being broken down especially into innocuous products by the action of living things. In an embodiment of the present invention the container may be a decomposable product in the environment.

A "Lid" refers to a portion of the container that may be opened to use the product which might have been filled in the container. In an embodiment of the present invention, the lid may be made of plastic or the alike.

A "Base" refers to a lower most portion of the container. In an embodiment of the present invention, the base may be a round base, a square base, or a rectangular base.

A "first segment" refers to a small segment in the lid that may store first pigment. In an embodiment of the present invention, the first segment may be made of aluminum. Furthermore this may be a breakable segment.

A "second segment" refers to refers to a small segment in the lid that may store second pigment. In an embodiment of the present invention, the first segment may be made of aluminum. Furthermore this may be a breakable segment.

A "First pigment" refers to a color pigment. In an embodiment of the present invention, the color pigment may be a pigment of any color.

A "Second pigment" refers to a bio-degrading agent. In an embodiment of the present invention, the bio-degrading agent may be a fungus as "pestalotiopsismicrosporia".

Referring to FIG. 1, a lid such as a lid 100 for covering the bio degradable container is depicted. The lid 100 comprises an upper cover 101 that may be made of plastic material. The upper cover may be a safeguard cover for rest of the components of the lid 100. All the components of the lid may be bio degradable components.

The lid further comprises a pullable seal tab 102. The pullable seal tab may be configured to break the barriers separating the segments.

In an embodiment of the present invention, the pullable seal tab 102 of a pre-determined length. The length may be determined based on the size of the lid, which may be based on the size of the bio degradable container. Furthermore, a pullable face of the pullable seal tab protrudes an upper cover of the lid.

In an embodiment of the present invention, In the event when the pullable seal tab 102 may be pulled, then the container may also gets locked. This feature ensures that the unattended container is safe as once the pullable seal tab 102 is pulled, apart from the breakage of the casing, the container also gets sealed so that nobody may further use it in any circumstances.

The lid further comprises a first segment 103. The first segment 103 may corresponds to a smaller segment that may hold the first pigment. The first pigment may correspond to a color pigment.

The lid further comprises a second segment 104. The second segment 104 may corresponds to a bigger segment that may hold the second pigment. The second pigment may further correspond to a bio-degrading agent.

The lid further comprises a breakable casing 105. The breakable casing may be made of aluminium. The aluminium based breakable casing may be a protective cover to the first segment and the second segment.

In an exemplary embodiment, if the aluminium based breakable casing is broken during transportation, then the color pigment and the bio-degrading agent may leak and the container may become unusable. This further prevents the use of the contaminated liquid, as the liquid in the container may change the color due to the leakage of colored pigment.

The lid further comprises a lower cover 106. The lower cover 106 may correspond to a weakest cover, which may break firstly upon pulling of a pullable seal tab. In an embodiment of the present invention, an inner portion of the lower cover engages the pullable seal tab with said breakable casing to release the first pigment and the second pigment to bio-degrade the container.

In an embodiment of the present invention, an inner portion of the lid has a spiral wrap construction. The number of spiral may be based on the size of the lid, which may be further based on the size of the container.

Figure 2:
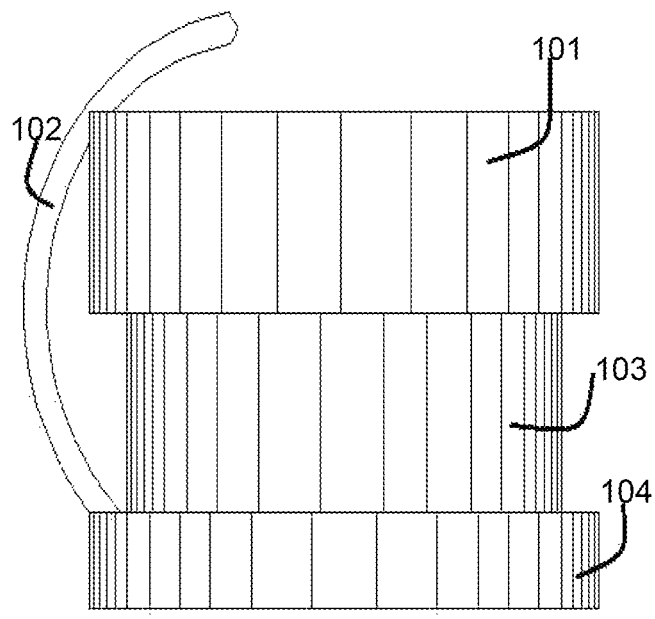
FIG. 2 depicts a side view of the various sections of the lid, in accordance with various embodiments of the present invention.
Figure 3:
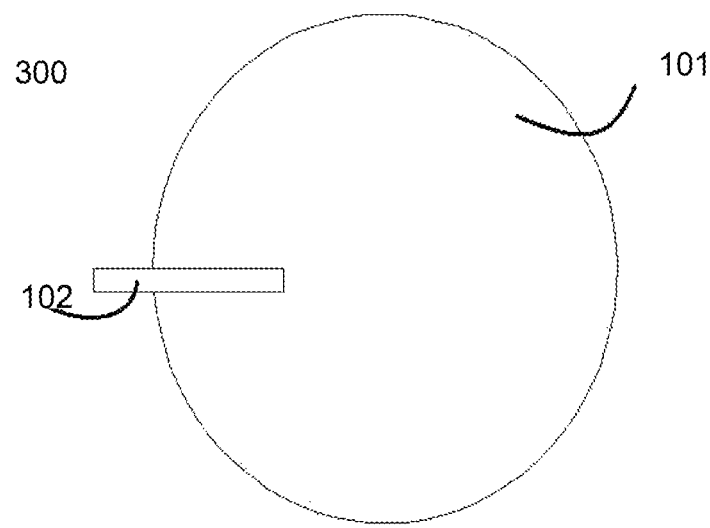
FIG. 3 depicts an outer shell of the lid, in accordance with various embodiments of the present invention.
Figure 4:
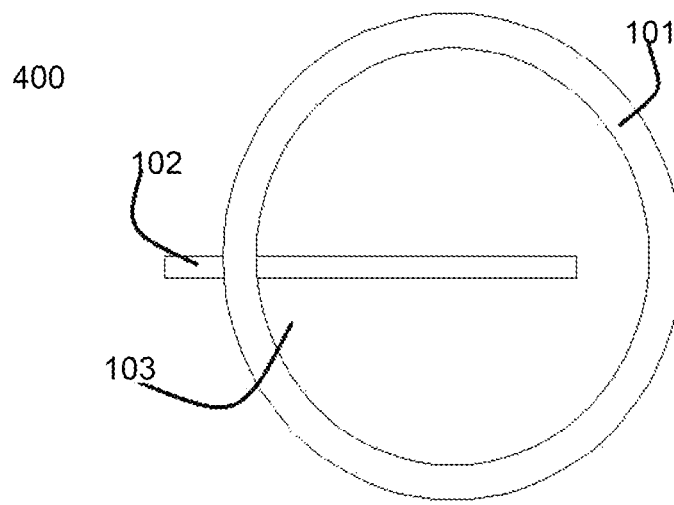
FIG. 4 depicts an exploded view of the bio-degradable container, in accordance with various embodiments of the present invention.
Figure 5:
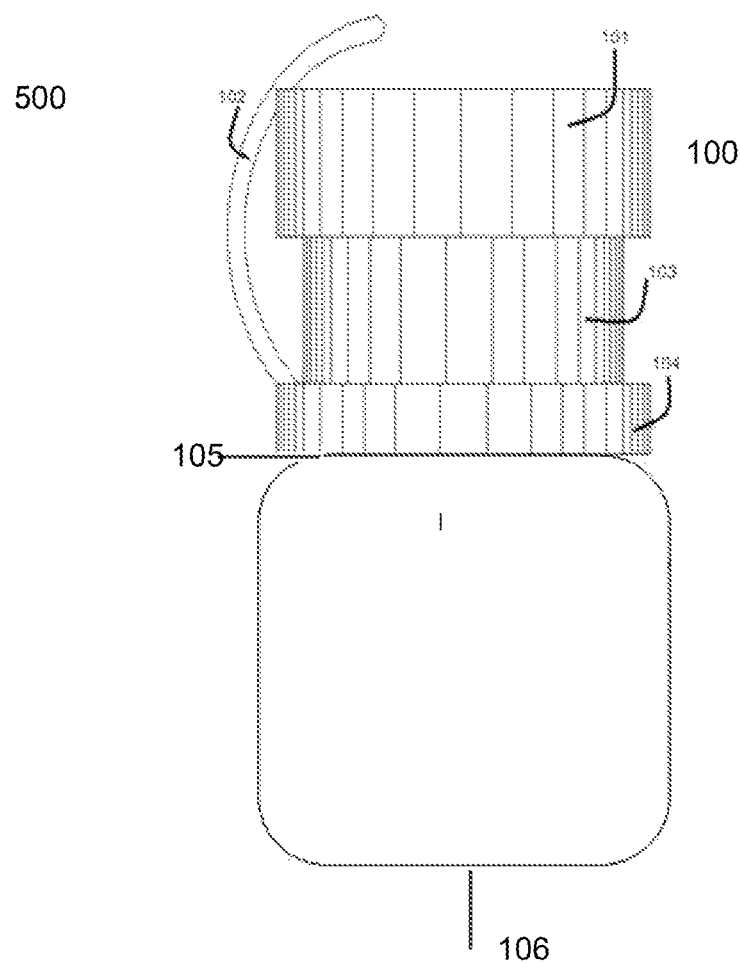
FIG. 5 depicts a complete view of the bio-degradable container, in accordance with various embodiments of the present invention.

FIG. 2 depicts a side view of the various sections of the lid, in accordance with various embodiments of the present invention. In an embodiment of the present invention, the lid of biodegradable cap is shown as 200. The lid 200 comprises an upper cover 101 that may be made of plastic material and may act as a protection for the top of the lid and it may also biodegrade with the rest of the lid. Further 102 may be the pullable seal tab that pulls out the aluminium that is supporting the fungus. Upon being pulled, the tab drops the fungus into the container. 103 may be the plastic shell of the aluminium compartment containing the fungi and the food colouring. Furthermore 104 may be the bottom layer of the cap. When the pullable seal tab is pulled, it serves as a trapdoor for the fungus to be released into the container.

FIG. 3 depicts an outer shell of the lid, in accordance with various embodiments of the present invention. In an embodiment of the present invention, the outer shell of biodegradable cap is shown as 300. The upper cover or the outer shell 101 of the lid may be made of plastic which may also biodegrade upon the fungi's release. 102 may correspond to pullable seal tab. When the container use has finished, the pullable seal tab will be pulled and it may lock the container and the container cannot be opened again.

FIG. 4 depicts an exploded view of the bio-degradable container as seen from above, in accordance with various embodiments of the present invention. In an embodiment of the present invention, the outer shell of biodegradable cap is shown as 400. The upper cover or the outer shell 101 of the lid may be made of plastic which may also biodegrade upon the fungi's release. 102 may correspond to pullable seal tab. When the container use has finished, the pullable seal tab will be pulled and it may lock the container and the container cannot be opened again. Further, the lid 100 comprising the first segment 103. The first segment 103 may corresponds to a smaller segment that may hold the first pigment. The first pigment may correspond to a color pigment.

FIG. 5 depicts a complete view of the bio-degradable container, in accordance with various embodiments of the present invention. As shown in FIG. 500, a round shaped container which has a lid. The lid such as a lid for covering the bio degradable container is depicted. The lid 100 comprises an upper cover 101 that may be made of plastic material. The upper cover may be a safeguard cover for rest of the components of the lid 100. All the components of the lid may be bio degradable components. The lid further comprises a pullable seal tab 102. The pullable seal tab may be configured to break the barriers separating the segments. In an embodiment of the present invention, the pullable seal tab 102 of a pre-determined length. The length may be determined based on the size of the lid, which may be based on the size of the bio degradable container.

Furthermore, a pullable face of the pullable seal tab protrudes an upper cover of the lid. In an embodiment of the present invention, In the event when the pullable seal tab 102 may be pulled, then the container may also gets locked. This feature ensures that the unattended container is safe as once the pullable seal tab 102 is pulled, apart from the breakage of the casing, the container also gets sealed so that nobody may further use it in any circumstances. The lid further comprises a first segment 103. The first segment 103 may corresponds to a smaller segment that may hold the first pigment. The first pigment may correspond to a color pigment. The lid further comprises a second segment 104. The second segment 104 may corresponds to a bigger segment that may hold the second pigment. The second pigment may further correspond to a bio-degrading agent.

The lid further comprises a breakable casing 105. The breakable casing may be made of aluminium. The aluminium based breakable casing may be a protective cover to the first segment and the second segment. Furthermore, the container comprises a body. The body of the container is the lower portion which may be utilized for storing the liquid or consumable item.

In an exemplary embodiment, if the aluminium based breakable casing is broken during transportation, then the color pigment and the bio-degrading agent may leak and the container may become unusable. This further prevents the use of the contaminated liquid, as the liquid in the container may change the color due to the leakage of colored pigment.

The lid further comprises a lower cover 106. The lower cover 106 may correspond to a weakest cover, which may break firstly upon pulling of a pullable seal tab. In an embodiment of the present invention, an inner portion of the lower cover engages the pullable seal tab with said breakable casing to release the first pigment and the second pigment to bio-degrade the container.

In an exemplary embodiment, the container may be made of paper or hard paper sheet. This enables the paper or the hard paper sheet to dissolve in the natural environment and the inner portion which may be made of plastic, may be consumed by the fungus which may get released upon breakage.

In an exemplary embodiment, to initiate the biodegradation of used container having biodegradable lid using "pestalotiopsismicrosporia" fixed on the container, all that is required is to pull the pullable seal tab coming out of the lid. When the pullable seal tab is pulled, which is connected to the aluminium casing separating the fungi from the container content, the pullable seal tab will break the aluminium seal of breakable first casing. The breaking of the seal after the bottle content being used, releases the fungi into the container to biodegrade it.

In the case of accidental brokerage of the breakable first casing during the filled bottle content the red food coloring stored along with fungus will indicate the brokerage as it will show the red color water after mixing with the content of the container. This will let people know that the water is not safe to drink. The lid is round, the ideal shape of a lid, and is made out of plastic from the outside. The container itself will be 22 cm tall, (being able to hold about 16.9 fluid ounces), with the plastic part of the cap having a diameter of approximately 2.5 centimeters and a height of 2 centimeters.

Inside the lid, there will be an aluminium casing that contains the plastic-consuming fungi. This aluminium casing will have a diameter of an estimated 2 centimeters and a height of 0.8 centimeters. The casing will keep the fungi from consuming the plastic outer layer of the cap. The lid also consists of a pullable seal tab, in which one of the ends will be attached to the base of the aluminium casing. Part of the pullable seal tab will protrude outside from the inside of the cap. When the pullable seal tab is pulled, it will break the bottom seal of the aluminium casing, allowing the fungi to be released into the empty bottle for disposal. The fungi will fully consume the plastic container within a matter of weeks. In the container, the lid is 3 times as high with about the same diameter as an ordinary bottle lid, to be able to contain the fungi and food dye. The invention could also have different types of colors of food dye. It can also use other materials to case the fungi.

In some embodiments, an inserted and bonded seamless liner protects the inside of the container. Preferably, the liner includes an organic, vegetable based and biodegradable plastic resin coating, which makes the liner water and air tight yet able to biodegrade into compostable material.

In some embodiments, a spiral wound liner protects the inside of the container. Preferably, the liner includes an organic, vegetable based and biodegradable plastic resin coating, which makes the liner water and air tight yet able to biodegrade into compostable material. The leading edge of the liner's winding may be folded back upon itself so that there is no cut edge of paper that would allow water to wick into the paper.

In one aspect, a container disclosed herein includes a top section that has provision for a connection to a threaded neck and a threaded mouth component, and a lower section with an integral bottom. The container may be formed by joining the top and lower sections. The container may be entirely compostable and/or recyclable. The top section may be a funnel section. The lower section may be a cylindrical section or a conical section. Inside and outside surfaces of the sections may be coated with a thin waterproof and biodegradable coating. The coating may be formed from one or more biodegradable plastic resin and a corn-based PLA plastic. The inner threaded cap may be detachably associated with the larger outer cap. The detachable association may include a pull tab. The container may further include a structural element for inserting the container to provide additional support for contents of the container.

In another aspect, a container disclosed herein is a biodegradable and/or recyclable container for storing semi-solid and liquid items such as beverages, water, oil-based creams, food products, lotions, medicines, wet chemicals, and the like. The container may be manufactured from a paper pulp material, and may have a biodegradable plastic resin coating on the inside and/or outside to protect it from exposure to air and moisture. The paper pulp may degrade into compost material when exposed to biodegrading influences, such as extreme biodegrading influences. The container may be sealed by a lid that may be used for re-closing the container for a short time after the container has been opened. Further, the lid may be secured to provide a water-resistant and air-resistant seal.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A bio-degradable container comprising:
   a body; and
   a lid; wherein said lid comprises:
   an upper cover;
   a pullable seal tab of a pre-determined length; wherein a pullable face of said pullable seal tab protrudes beyond said upper cover;
   a breakable casing on a lower side of said upper cover, wherein said breakable casing comprises a first segment and a second segment; and
   a lower cover, wherein an inner portion of said lower cover engages said pullable seal tab with said breakable casing to release a first pigment and a second pigment to bio-degrade said container.

2. The bio-degradable container as claimed in claim 1, wherein said body further comprises a base portion.

3. The bio-degradable container as claimed in claim 1, wherein an inner portion of said lid has a spiral wrap construction.

4. The bio-degradable container as claimed in claim 1, wherein said first segment houses said first pigment.

5. The bio-degradable container as claimed in claim 4, wherein said first pigment is a color pigment.

6. The bio-degradable container as claimed in claim 1, wherein said second segment houses said second pigment.

7. The bio-degradable container as claimed in claim 6, wherein said second pigment is a bio-degrading agent.

8. The bio-degradable container as claimed in claim 6, wherein said second segment is an aluminium segment.

9. The bio-degradable container as claimed in claim 1, wherein said breakable casing is a plastic casing.

10. The bio-degradable container as claimed in claim 1, wherein said breakable casing is an aluminum casing.

11. The bio-degradable container as claimed in claim 1, wherein said pullable seal tab is further configured to lock said body.

12. The bio-degradable container as claimed in claim 11, wherein the said locking to said body is actuated by pulling of said pullable seal tab.

\* \* \* \* \*